US009848909B2

(12) United States Patent
Bae et al.

(10) Patent No.: US 9,848,909 B2
(45) Date of Patent: Dec. 26, 2017

(54) AUTOMATIC HAIR TRANSPLANTER FOR TRANSPLANTING FOLLICLES

(71) Applicants: ELECTRONICS AND TELECOMMUNICATIONS RESEARCH INSTITUTE, Daejeon (KR); KYUNGPOOK NATIONAL UNIVERSITY INDUSTRY-ACADEMIC COOPERATION FOUNDATION, Daegu (KR)

(72) Inventors: Tae Wuk Bae, Daegu (KR); Kyu Hyung Kim, Daegu (KR); Moon Kyu Kim, Daegu (KR); Jung Chul Kim, Daegu (KR); Jung Wook Suh, Daegu (KR); Soo In Lee, Daejeon (KR); Hyung Soo Lee, Daegu (KR); Yong Chul Jung, Daegu (KR); Eun Chang Choi, Daegu (KR); Dae Sik Kim, Daejeon (KR); Chang Hyuk Hong, Daegu (KR)

(73) Assignees: ELECTRONICS AND TELECOMMUNICATIONS RESEARCH INSTITUTE, Daejeon (KR); KYUNGPOOK NATIONAL UNIVERSITY INDUSTRY-ACADEMIC COOPERATION FOUNDATION, Daegu (KR)

( * ) Notice: Subject to any disclaimer, the term of this patent is extended or adjusted under 35 U.S.C. 154(b) by 52 days.

(21) Appl. No.: 15/163,527

(22) Filed: May 24, 2016

(65) Prior Publication Data

US 2017/0020566 A1  Jan. 26, 2017

(30) Foreign Application Priority Data

Jul. 22, 2015 (KR) ........................ 10-2015-0103800

(51) Int. Cl.
*A61B 17/34* (2006.01)
*A61B 17/3205* (2006.01)
(Continued)

(52) U.S. Cl.
CPC .... *A61B 17/3468* (2013.01); *A61B 17/32053* (2013.01); *A61B 2017/00752* (2013.01);
(Continued)

(58) Field of Classification Search
CPC .......... A61B 17/3468; A61B 17/32053; A61B 2017/00969; A61B 2017/320064
(Continued)

(56) References Cited

U.S. PATENT DOCUMENTS 4,216,777 A * 8/1980 Pridemore ................ A61F 2/10
606/186
5,417,683 A * 5/1995 Shiao .................. A61B 17/3468
604/173
(Continued)

FOREIGN PATENT DOCUMENTS

KR  20-0470718 Y1  1/2014

*Primary Examiner* — Melanie Tyson

(57) ABSTRACT

Provided is an automatic hair transplanter for transplanting follicles including a housing having a space therein and having an aperture in a front surface, a cartridge installed behind the aperture and having a plurality of holes containing each of needle and rod assemblies, a cartridge driver configured to sequentially cause centers of the needle and rod assemblies to correspond to the center of the aperture by causing the cartridge to make a rectilinear motion or a rotary motion, a needle-and-rod assembly pressurizer configured to pressurize the back end of a needle and rod assembly whose center corresponds to the center of the aperture, and a manipulator having a switch for controlling operations of the cartridge mover and the needle-and-rod assembly pressurizer.

13 Claims, 4 Drawing Sheets

(51) Int. Cl.
 *A61B 17/00* (2006.01)
 *A61B 17/32* (2006.01)
(52) U.S. Cl.
 CPC ............... *A61B 2017/00969* (2013.01); *A61B 2017/320064* (2013.01)
(58) Field of Classification Search
 USPC ........................................................ 606/187
 See application file for complete search history.

(56) References Cited

U.S. PATENT DOCUMENTS

| | | | |
|---|---|---|---|
| 5,643,308 A * | 7/1997 | Markman | A61B 17/3468 606/1 |
| 8,211,134 B2 | 7/2012 | Oostman, Jr. | |
| 2003/0097144 A1 | 5/2003 | Lee | |

* cited by examiner

AUTOMATIC HAIR TRANSPLANTER FOR TRANSPLANTING FOLLICLES

CROSS-REFERENCE TO RELATED APPLICATION

This application claims priority to and the benefit of Korean Patent Application No. 10-2015-0103800, filed on Jul. 22, 2015, the disclosure of which is incorporated herein by reference in its entirety.

BACKGROUND

1. Field of the Invention

The present invention relates to a hair transplanter for transplanting follicles, and more particularly, to an automatic hair transplanter for transplanting follicles which enables a reduction in the time taken for follicle transplantation and also the minimization of transplantation operator fatigue in a follicle transplantation process.

2. Discussion of Related Art

A large number of people suffer from alopecia, that is, excessive loss of hair, such as the hair on one's head. Here, a region of hair loss is remarkably shown compared to a region of no hair loss. Therefore, some alopecia patients wear wigs for beauty, thereby preventing regions of hair loss from being remarkably shown.

However, it is inconvenient to wear and manage a wig, and a wig does not harmonize with existing hair and thus is followed by the sense of difference. Also, a region on which a wig can be put is limited.

For these reasons, alopecia patients who have hair transplantation in regions of hair loss are increasing lately.

Since hair transplantation results in long-term maintenance of the effect of covering a region of hair loss and no sense of difference from existing hair, the number of alopecia patients who consider hair transplantation is constantly increasing.

Meanwhile, a manual hair transplanter for transplanting follicles is generally used in a hair transplantation procedure.

An existing manual hair transplanter for transplanting follicles includes a needle containing a follicle and a rod for pressurizing the follicle contained in the needle. In the process of inserting the needle containing the follicle into skin and then withdrawing the needle, the follicle is transplanted into the skin by pressurizing the follicle inserted into the skin with the rod.

Using such an existing manual hair transplanter for transplanting follicles, it is possible to transplant a follicle in a region of hair loss. However, only one follicle is transplanted through one needle, and thus it takes a considerable time to transplant hundreds to thousands of follicles in a region of hair loss.

Also, in the case of the existing manual hair transplanter for transplanting follicles, a body containing the needle is lifted by a transplantation operator's hand work, that is, with the transplantation operator's thumb, index finger, etc., to withdraw the needle. Therefore, when transplanting hundreds to thousands of follicles into a region of hair loss, the transplantation operator feels considerable fatigue due to repeated hand works, and transplantation operators who work for a long period may suffer from a musculoskeletal disease.

For the aforementioned reasons, development of an automatic hair transplanter for transplanting follicles which enables a reduction in the time taken for follicle transplantation and also the minimization of transplantation operator fatigue in a follicle transplantation process is under way in the corresponding field, but satisfactory results have not been obtained so far.

SUMMARY OF THE INVENTION

The present invention is directed to providing an automatic hair transplanter for transplanting follicles which enables a reduction in the time taken for follicle transplantation and also the minimization of transplantation operator fatigue in a follicle transplantation process.

According to an aspect of the present invention, there is provided an automatic hair transplanter for transplanting follicles, the automatic hair transplanter including: a housing having a space therein and having an aperture in a front surface; a cartridge installed behind the aperture and in which a plurality of holes containing each of needle and rod assemblies are formed; a cartridge driver configured to sequentially cause centers of the needle and rod assemblies to correspond to a center of the aperture by causing the cartridge to make a rectilinear motion or a rotary motion; a needle-and-rod assembly pressurizer configured to pressurize a back end of a needle and rod assembly whose center corresponds to the center of the aperture; and a manipulator having a switch for controlling operations of the cartridge driver and the needle-and-rod assembly pressurizer.

The housing may be formed to be divisible into upper and lower parts or left and right parts.

The housing may have a holder for installing the cartridge.

The cartridge may be formed in a straight-line shape in which the plurality of holes containing each of the needle and rod assemblies are disposed in one line.

The cartridge may be formed in a cylindrical shape in which the plurality of holes containing each of the needle and rod assemblies are disposed in a circular shape.

Each of the needle and rod assemblies may include a needle whose front end contains a follicle, a rod inserted into the needle, a first elastic body configured to elastically support the needle, and a second elastic body configured to elastically support the rod.

The first elastic body may have a lower elasticity than the second elastic body.

The cartridge driver may include a motor configured to rotate upon application of power, a driving gear coupled to a shaft of the motor, and a driven gear coupled to the cartridge and engaged with the driving gear.

The cartridge driver may cause the cartridge of the straight-line shape to make the rectilinear motion.

The cartridge driver may cause the cartridge of the cylindrical shape to make the rotary motion.

The needle-and-rod assembly pressurizer may include a motor configured to rotate upon application of power, a screw configured to rotate by the rotation of the motor, a moving block threadedly engaged with the screw, and a pressurization shaft coupled to the moving block.

A center of the pressurization shaft may correspond to the center of the aperture.

The manipulator may be disposed on an outer surface of the housing.

BRIEF DESCRIPTION OF THE DRAWINGS

The above and other objects, features and advantages of the present invention will become more apparent to those of ordinary skill in the art by describing in detail exemplary embodiments thereof with reference to the accompanying drawings, in which.

DETAILED DESCRIPTION OF EXEMPLARY EMBODIMENTS

Advantages and features of the present invention and a method of achieving the same will be more clearly understood from embodiments described below in detail with reference to the accompanying drawings. However, the present invention is not limited to the following embodiments and may be implemented in various different forms. The embodiments are provided merely for complete disclosure of the present invention and to fully convey the scope of the invention to those of ordinary skill in the art to which the present invention pertains. The present invention is defined only by the scope of the claims.

Meanwhile, the terminology used herein is for the purpose of describing the embodiments and is not intended to be limiting of the invention. As used in this specification, the singular form of a word includes the plural unless the context clearly indicates otherwise. The term "comprise" and/or "comprising," when used herein, does not preclude the presence or addition of one or more components, steps, operations, and/or elements other than stated components, steps, operations, and/or elements. Hereinafter, exemplary embodiments of the present invention will be described in detail with reference to the accompanying drawings.

Figure 1:
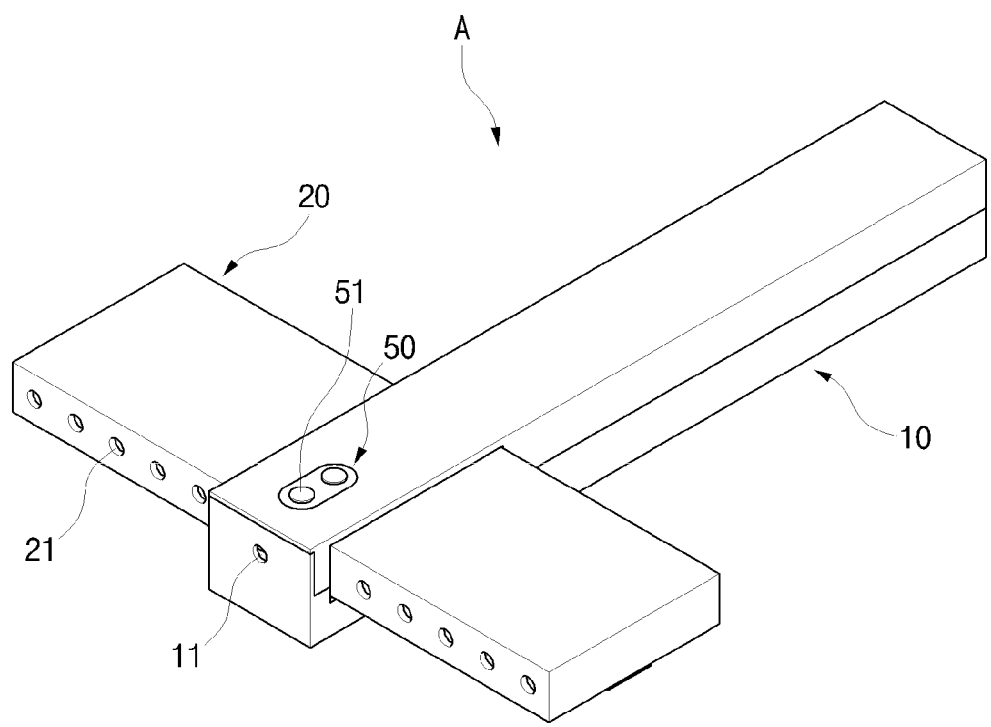
FIG. 1 is an outer perspective view of an automatic hair transplanter for transplanting follicles according to an exemplary embodiment of the present invention.
Figure 2:
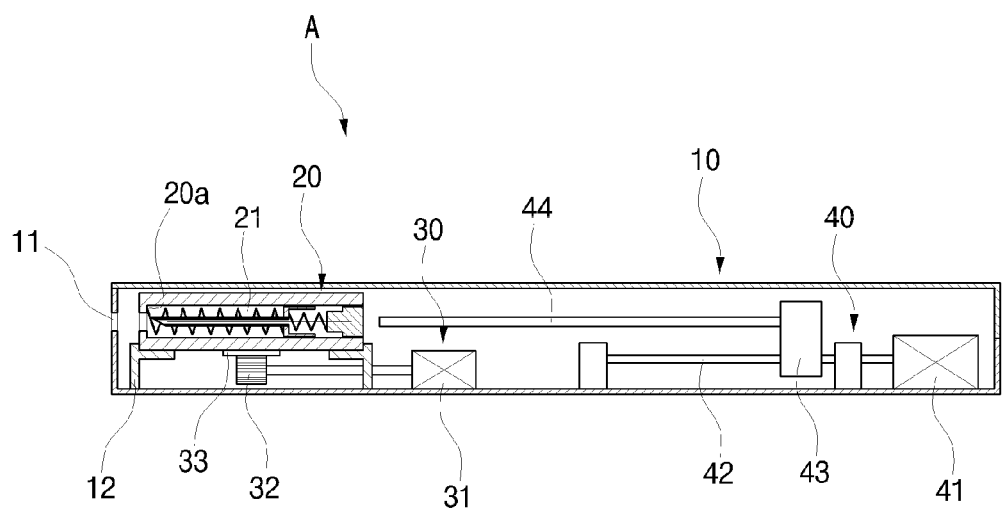
FIG. 2 is a cross-sectional view illustrating a structure of an automatic hair transplanter for transplanting follicles according to an exemplary embodiment of the present invention.

As shown in FIGS. 1 and 2, an automatic hair transplanter A for transplanting follicles according to an exemplary embodiment of the present invention includes a housing 10, a cartridge 20, a cartridge driver 30, a needle-and-rod assembly pressurizer 40, and a manipulator 50.

The housing 10 has a space therein, and has an aperture 11 in the front surface.

Since the housing 10 has the space therein, the cartridge 20, the cartridge driver 30, and the needle-and-rod assembly pressurizer 40 may be disposed in the housing 10. Also, since the housing 10 has the aperture 11 in the front surface, a needle and rod assembly 100 contained in the cartridge 20 may protrude from the housing 10 through the aperture 11.

This housing 10 may be formed to be divisible into upper and lower parts or left and right parts.

Since the housing 10 is formed to be divisible into the upper and lower parts or the left and right parts, when the housing 10 is divided into the upper and lower parts or the left and right parts, the cartridge 20, the cartridge driver 30, and the needle-and-rod assembly pressurizer 40 may be disposed in the housing 10.

The housing 10 may have a holder 12 for installing the cartridge 20.

Since the housing 10 has the holder 12 for installing the cartridge 20, it is possible to install the cartridge 20 in the housing 10 by support of the holder 12.

The cartridge 20 is installed behind the aperture 11, and has a plurality of holes 21 containing each of the needle and rod assemblies 100.

Since the cartridge 20 is installed behind the aperture 11 and has the plurality of holes 21 containing each of the needle and rod assemblies 100, when the needle and rod assemblies 100 contained in the holes 21 sequentially protrude from the housing 10 through the aperture 11, it is possible to continuously transplant as many follicles 200 as the number of the needle and rod assemblies 100.

Figure 3:
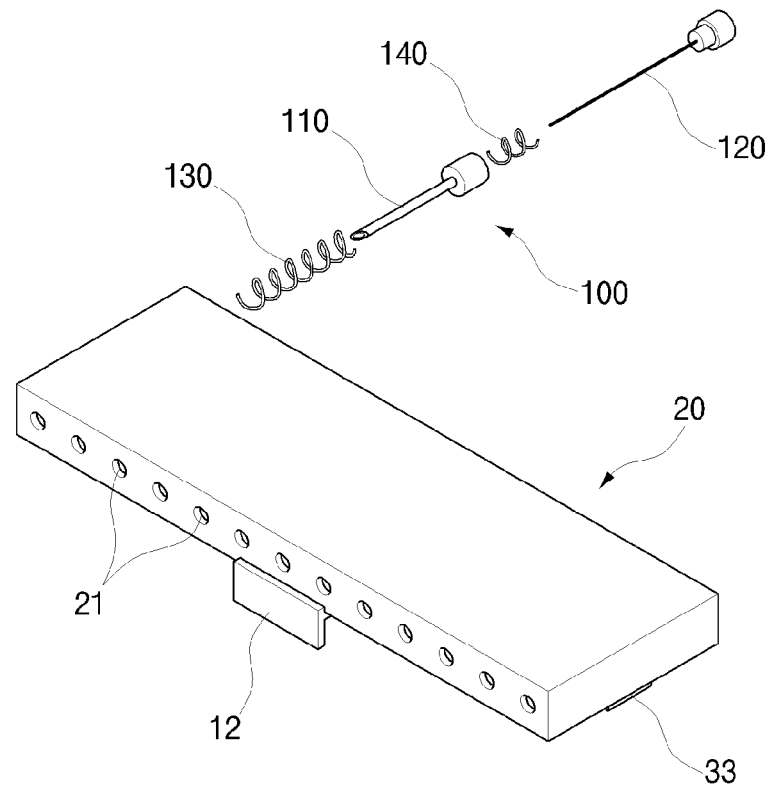
FIG. 3 is perspective view of a shape of a cartridge according to an exemplary embodiment of the present invention.

This cartridge 20 may be formed in a straight-line shape in which the plurality of holes 21 containing each of the needle and rod assemblies 100 are disposed in one line as shown in FIG. 3.

In the process of the cartridge 20 formed in the straight-line shape being moved in a lateral direction by the cartridge driver 30, the plurality of needle and rod assemblies 100 sequentially protrude from the housing 10 through the aperture 11.

Figure 4:
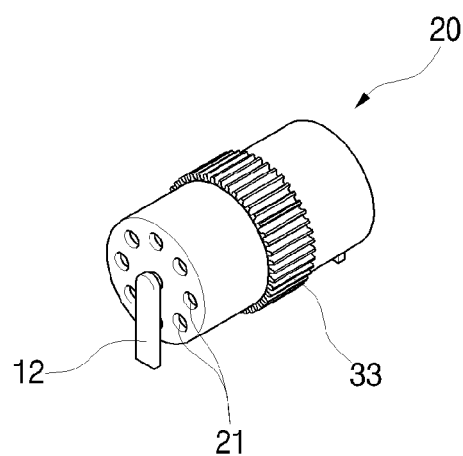
FIG. 4 is perspective view of another shape of a cartridge according to an exemplary embodiment of the present invention.

Also, the cartridge 20 may be formed in a cylindrical shape in which the plurality of holes 21 containing each of the needle and rod assemblies 100 are disposed in a circular shape as shown in FIG. 4.

In the process of the cartridge 20 formed in the circular shape being rotated by the cartridge driver 30, the plurality of needle and rod assemblies 100 sequentially protrude from the housing 10 through the aperture 11.

A part of the cartridge 20 formed in the cylindrical shape may be exposed to the outside of the housing 10.

When a part of the cartridge 20 formed in the cylindrical shape is exposed to the outside of the housing 10, the thickness of the housing 10 is minimized.

Each of the holes 21 has a sill 20a in its front end.

Since each of the holes 21 has a sill 20a in its front end, the front end of a first elastic body 130 which will be described below comes in contact with the sill 20a, and the leaving of the first elastic body 130 from the hole 21 is prevented.

Meanwhile, each of the needle and rod assemblies 100 includes a needle 110 containing a follicle 200 in its front end, and a rod 120 inserted into the needle 110.

Since each of the needle and rod assemblies 100 includes a needle 110 containing a follicle 200 in its front end and a rod 120 inserted into the needle 110, when the needle 110 protrudes from the housing 10 and is inserted into skin, the follicle 200 is placed in the skin, and when the rod 120 protrudes from the housing 10, the follicle 200 is stably embedded in the skin.

Figure 8:
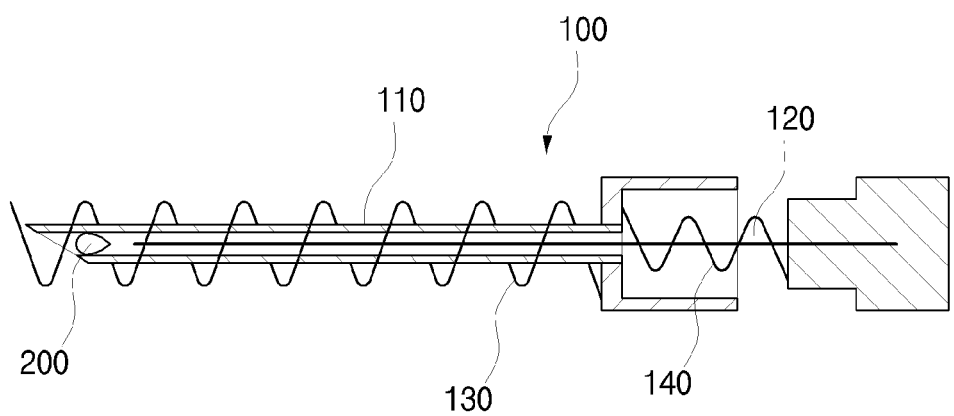
FIG. 8 is an exploded cross-sectional view illustrating a structure of a needle and rod assembly according to an exemplary embodiment of the present invention.

As shown in FIG. 8, each of the needle and rod assemblies 100 further includes a first elastic body 130 which elastically supports a needle 110, and a second elastic body 140 which elastically supports a rod 120.

Since each of the needle and rod assemblies 100 further includes a first elastic body 130 elastically supporting a needle 110, and a second elastic body 140 elastically supporting a rod 120, the needle 110 protrudes from the housing 10 by contraction of the first elastic body 130, and the rod 120 protrudes from the housing 10 by contraction of the second elastic body 140. Here, the first elastic body 130 has a lower elasticity than the second elastic body 140.

Since the first elastic body 130 has a lower elasticity than the second elastic body 140, when the needle and rod assembly 100 is pressurized by the needle-and-rod assembly pressurizer 40, the first elastic body 130 having a relatively low elasticity is rapidly contracted compared to the second elastic body 140, so that the needle 110 rapidly protrudes from the housing 10 compared to the rod 120, and the second elastic body 140 having a relatively high elasticity is slowly contracted compared to the first elastic body 130, so that the rod 120 slowly protrudes from the housing 10 compared to the needle 110.

The cartridge driver 30 sequentially causes the centers of the needle and rod assemblies 100 to correspond to the center of the aperture 11 by causing the cartridge 20 to make a rectilinear motion or a rotary motion.

Since the cartridge driver 30 sequentially causes the centers of the needle and rod assemblies 100 to correspond to the center of the aperture 11 by causing the cartridge 20 to make a rectilinear motion or a rotary motion, when the needle and rod assemblies 100 whose centers correspond to the center of the aperture 11 are sequentially pressurized to protrude, follicles 200 contained in each of the needle and rod assemblies 100 are continuously transplanted into skin.

This cartridge driver 30 includes a motor 31 which rotates upon application of the power, a driving gear 32 coupled to a shaft (not shown) of the motor 31, and a driven gear 33 coupled to the cartridge 20 and engaged with the driving gear 32.

Since the cartridge driver 30 includes the motor 31 rotating upon application of the power, the driving gear 32 coupled to the shaft of the motor 31, and the driven gear 33 coupled to the cartridge 20 and engaged with the driving gear 32, when the torque of the motor 31 is transferred to the cartridge 20 through the driving gear 32 and the driven gear 33, the cartridge 20 may make a rectilinear motion or a rotary motion.

Here, when the driven gear 33 is linearly disposed on the cartridge 20 of the straight-line shape, the cartridge 20 of the straight-line shape makes a rectilinear motion, that is, moves in a lateral direction on the holder 12, and when the driven gear 33 is disposed in a circular shape on the cartridge 20 of the circular shape, the cartridge 20 of the circular shape makes a rotary motion, that is, rotates on the holder 12.

The needle-and-rod assembly pressurizer 40 pressurizes the back end of a needle and rod assembly 100 whose center corresponds to the center of the aperture 11.

Since the needle-and-rod assembly pressurizer 40 pressurizes the back end of the needle and rod assembly 100 whose center corresponds to the center of the aperture 11, the needle 110 and the rod 120 may protrude from the housing 10.

This needle-and-rod assembly pressurizer 40 includes a motor 41 which rotates upon application of the power, a screw 42 which rotates by the rotation of the motor 41, a moving block 43 which is threadedly engaged with the screw 42, and a pressurization shaft 44 coupled to the moving block 43.

Since the needle-and-rod assembly pressurizer 40 includes the motor 41 rotating upon application of the power, the screw 42 rotating by the rotation of the motor 41, the moving block 43 threadedly engaged with the screw 42, and the pressurization shaft 44 coupled to the moving block 43, the screw 42 rotates by operation of the motor 41, and the moving block 43 moves by the rotation of the screw 42. When the front end of the pressurization shaft 44 comes in contact with the back end of a needle and rod assembly 100 accordingly, it is possible to pressurize the needle and rod assembly 100. Here, the center of the pressurization shaft 44 corresponds to the center of the aperture 11.

Since the center of the pressurization shaft 44 corresponds to the center of the aperture 11, the needle and rod assembly 100 whose center corresponds to the center of the aperture 11 may protrude from the housing 10 through the aperture 11 by forward movement of the pressurization shaft 44.

The manipulator 50 has a switch 51 for controlling operations of the cartridge driver 30 and the needle-and-rod assembly pressurizer 40.

Since the manipulator 50 has the switch 51 for controlling the operations of the cartridge driver 30 and the needle-and-rod assembly pressurizer 40, it is possible to control the cartridge driver 30 and the needle-and-rod assembly pressurizer 40 through manipulation of the switch 51. Here, the manipulator 50 is disposed on the outer surface of the housing 10.

Since the manipulator 50 is disposed on the outer surface of the housing 10, it is possible to manipulate the manipulator 50 while grabbing the housing 10.

Transplantation of a follicle 200 through the automatic hair transplanter A for transplanting follicles according to an exemplary embodiment of the present invention will be described in detail below.

In an exemplary embodiment of the present invention, the cartridge 20 having the plurality of holes 21 containing each of the needle and rod assemblies 100 is installed behind the aperture 11 of the housing 10.

Here, any one of the plurality of needle and rod assemblies 100 contained in the cartridge 20, in particular, a foremost needle and rod assembly 100 in the cartridge 20 of a straight-line shape, has a center corresponding to the center of the aperture 11 provided in the front surface of the housing 10.

In the housing 10, the needle-and-rod assembly pressurizer 40 which pressurizes the needle and rod assembly 100 whose center corresponds to the center of the aperture 11 is provided.

Therefore, when the back end of the needle and rod assembly 100 whose center corresponds to the center of the aperture 11 is pressurized by the needle-and-rod assembly pressurizer 40, the needle and rod assembly 100 protrudes from the housing 10. Here, the needle-and-rod assembly pressurizer 40 is operated by manipulation of the switch 51 of the manipulator 50 disposed on the outer surface of the housing 10.

Figure 7:
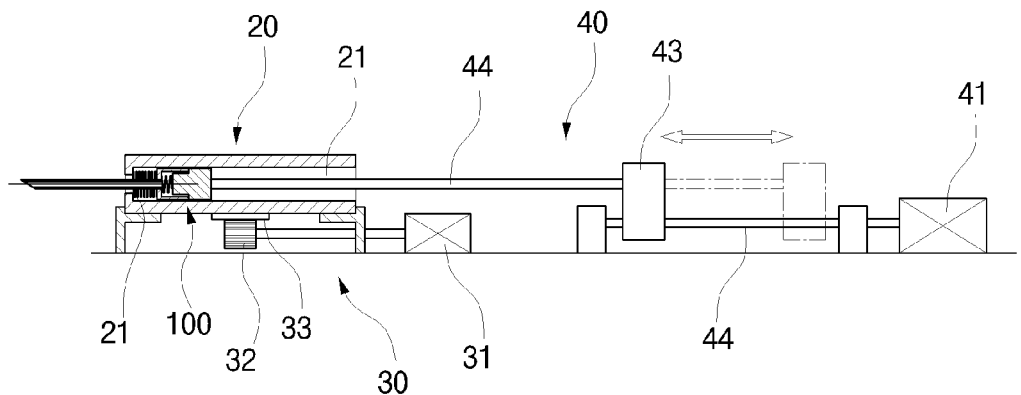
FIG. 7 is an example diagram illustrating pressurization of a needle and rod assembly caused by a needle-and-rod assembly pressurizer according to an exemplary embodiment of the present invention.

In other words, the motor 41 is operated by manipulating the switch 51 for operating the needle-and-rod assembly pressurizer 40 in the manipulator 50, and the screw 42 rotates due to the operation of the motor 41. Then, the moving block 43 threadedly engaged with the screw 42 moves forward, and the pressurization shaft 44 coupled to the moving block 43 moves forward due to the forward movement of the moving block 43 and pushes the back end of the needle and rod assembly 100. Therefore, as shown in FIG. 7, the needle and rod assembly 100 protrudes from the housing 10 due to the operation of the needle-and-rod assembly pressurizer 40.

In an exemplary embodiment of the present invention, since the first elastic body 130 elastically supporting the needle 110 has a lower elasticity than the second elastic body 140 elastically supporting the rod 120, when the needle and rod assembly 100 is pressurized by the needle-and-rod assembly pressurizer 40, the first elastic body 130 having a relatively low elasticity is rapidly contracted compared to the second elastic body 140, so that the needle 110 rapidly protrudes from the housing 10 compared to the rod 120, and the second elastic body 140 having a relatively high elasticity is slowly contracted compared to the first elastic body 130, so that the rod 120 slowly protrudes from the housing 10 compared to the needle 110.

Therefore, when the needle and rod assembly 100 is pressurized while the aperture 11 is in contact with skin in a region of hair loss, a follicle 200 contained in the front end of the needle 110 is placed in the skin and then pressurized by the rod 120, so that the follicle 200 is stably embedded in the skin. Here, the cartridge 20 is formed in a straight-line shape or a cylindrical shape and makes a rectilinear motion or a rotary motion by the cartridge driver 30.

Figure 5:
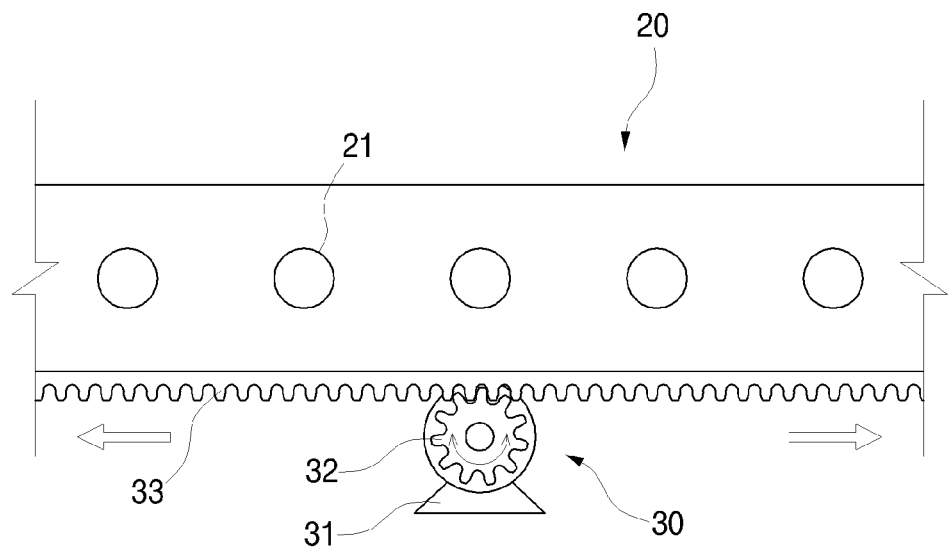
FIG. 5 is an example diagram illustrating a rectilinear motion of a linear cartridge caused by a cartridge driver according to an exemplary embodiment of the present invention.

In other words, as shown in FIG. 5, when the torque of the motor 31 is transferred to the driving gear 32 and the driven gear 33, the cartridge 20 of a straight-line shape is moved in a lateral direction on the holder 12, so that the centers of needle and rod assemblies 100 contained in each of the holes 21 sequentially correspond to the center of the aperture 11.

Therefore, when the centers of the needle and rod assemblies 100 contained in the cartridge 20 of a straight-line shape sequentially correspond to the center of the aperture 11, the needle and rod assemblies 100 are sequentially pressurized by the needle-and-rod assembly pressurizer 40, and thus it is possible to continuously transplant as many follicles 200 as the number of the needle and rod assemblies 100.

Figure 6:
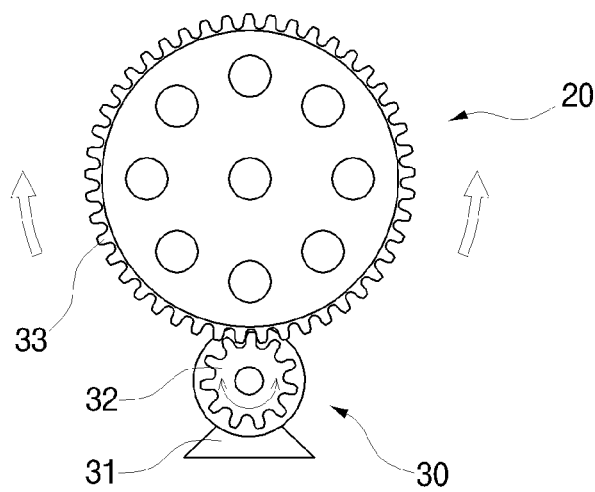
FIG. 6 is an example diagram illustrating a rotary motion of a cylindrical cartridge caused by a cartridge driver according to an exemplary embodiment of the present invention.

Also, as shown in FIG. 6, when the torque of the motor 31 is transferred to the driving gear 32 and the driven gear 33, the cartridge 20 of a cylindrical shape rotates on the holder 12, so that the centers of needle and rod assemblies 100 contained in each of the holes 21 sequentially correspond to the center of the aperture 11.

Therefore, when the centers of the needle and rod assemblies 100 contained in the cartridge 20 of a cylindrical shape sequentially correspond to the center of the aperture 11, the needle and rod assemblies 100 are sequentially pressurized by the needle-and-rod assembly pressurizer 40, and thus it is possible to continuously transplant as many follicles 200 as the number of the needle and rod assemblies 100.

Meanwhile, the cartridge driver 30 is also operated by manipulation of the switch 51 of the manipulator 50 disposed on the outer surface of the housing 10.

In other words, when the switch 51 for operating the cartridge driver 30 is manipulated in the manipulator 50, the motor 31 rotates, and the driving gear 32 rotates by the rotation of the motor 31, so that the torque of the motor 31 is transferred to the driven gear 33.

Since the cartridge driver 30 is also operated in this way by manipulation of the switch 51 of the manipulator 50 disposed on the outer surface of the housing 10, a transplantation operator is not required to do a hand work except to manipulate the switch 51 of the manipulator 50 in the process of transplanting the follicles 200. In other words, in the process of transplanting the follicles 200, hand works of the transplantation operator may be minimized, and transplantation operator fatigue is minimized.

According to the inventive automatic hair transplanter A for transplanting follicles, the plurality of needle and rod assemblies 100 are contained in the cartridge 20, and the centers of the needle and rod assemblies 100 sequentially correspond to the center of the aperture 11 of the housing 10 by a rectilinear motion or a rotary motion of the cartridge 20 caused by the cartridge driver 30. Also, a needle and rod assembly 100 whose center corresponds to the center of the aperture 11 of the housing 10 is pressurized by the needle-and-rod assembly pressurizer 40 and protrudes from the housing 10. Therefore, it is possible to continuously transplant follicles 200 contained in each of the plurality of needle and rod assemblies 100. Consequently, it is possible to reduce the time taken to transplant the follicles 200 and also minimize transplantation operator fatigue in the process of transplanting the follicles 200.

It will be apparent to those skilled in the art that various modifications can be made to the above-described exemplary embodiments of the present invention without departing from the spirit or scope of the invention. Thus, it is intended that the present invention covers all such modifications provided they come within the scope of the appended claims and their equivalents.

What is claimed is:

1. An automatic hair transplanter for transplanting follicles, the automatic hair transplanter comprising:
   a housing having a space therein and having an aperture in a front surface;
   a cartridge installed behind the aperture and in which a plurality of holes containing each of needle and rod assemblies are formed;
   a cartridge driver configured to sequentially cause centers of the needle and rod assemblies to correspond to a center of the aperture by causing the cartridge to make a rectilinear motion or a rotary motion;
   a needle-and-rod assembly pressurizer configured to pressurize a back end of a needle and rod assembly whose center corresponds to the center of the aperture; and
   a manipulator having a switch for controlling operations of the cartridge driver and the needle-and-rod assembly pressurizer.

2. The automatic hair transplanter of claim 1, wherein the housing is formed to be divisible into upper and lower parts or left and right parts.

3. The automatic hair transplanter of claim 1, wherein the housing has a holder for installing the cartridge.

4. The automatic hair transplanter of claim 1, wherein the cartridge is formed in a straight-line shape in which the plurality of holes containing each of the needle and rod assemblies are disposed in one line.

5. The automatic hair transplanter of claim 4, wherein the cartridge driver causes the cartridge of the straight-line shape to make the rectilinear motion.

6. The automatic hair transplanter of claim 1, wherein the cartridge is formed in a cylindrical shape in which the plurality of holes containing each of the needle and rod assemblies are disposed in a circular shape.

7. The automatic hair transplanter of claim 6, wherein the cartridge driver causes the cartridge of the cylindrical shape to make the rotary motion.

8. The automatic hair transplanter of claim 1, wherein each of the needle and rod assemblies includes:
   a needle whose front end contains a follicle;
   a rod inserted into the needle;
   a first elastic body configured to elastically support the needle; and
   a second elastic body configured to elastically support the rod.

9. The automatic hair transplanter of claim 8, wherein the first elastic body has a lower elasticity than the second elastic body.

10. The automatic hair transplanter of claim 1, wherein the cartridge driver includes:
   a motor configured to rotate upon application of power;
   a driving gear coupled to a shaft of the motor; and
   a driven gear coupled to the cartridge and engaged with the driving gear.

11. The automatic hair transplanter of claim 1, wherein the needle-and-rod assembly pressurizer includes:
   a motor configured to rotate upon application of power;
   a screw configured to rotate by the rotation of the motor;
   a moving block threadedly engaged with the screw; and
   a pressurization shaft coupled to the moving block.

12. The automatic hair transplanter of claim 11, wherein a center of the pressurization shaft corresponds to the center of the aperture.

13. The automatic hair transplanter of claim 1, wherein the manipulator is disposed on an outer surface of the housing.

* * * * *